United States Patent
Prass et al.

(10) Patent No.: US 6,292,701 B1
(45) Date of Patent: Sep. 18, 2001

(54) BIPOLAR ELECTRICAL STIMULUS PROBE WITH PLANAR ELECTRODES

(75) Inventors: Richard L. Prass, Virginia Beach, VA (US); David C. Hacker, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 09/362,891

(22) Filed: Jul. 29, 1999

Related U.S. Application Data

(60) Provisional application No. 60/096,243, filed on Aug. 12, 1998.

(51) Int. Cl.[7] .................................. A61N 1/04; A61N 1/05
(52) U.S. Cl. ......................... 607/116; 607/150; 607/145
(58) Field of Search .................................. 607/115, 116, 607/145, 149, 150

(56) References Cited

U.S. PATENT DOCUMENTS

| | | |
|---|---|---|
| 3,664,329 | 5/1972 | Naylor . |
| 3,830,226 | 8/1974 | Staub et al. . |
| 4,892,105 | 1/1990 | Prass . |
| 4,962,766 | 10/1990 | Herzon . |
| 5,161,533 | 11/1992 | Prass et al. . |
| 5,170,788 * | 12/1992 | Blumnfeld ........................... 128/642 |
| 5,569,242 * | 10/1996 | Lax et al. ............................... 606/42 |
| 5,741,250 * | 4/1998 | Garito et al. .......................... 606/45 |
| 6,090,104 * | 7/2000 | Webster, Jr. .......................... 606/41 |
| 6,156,060 * | 12/2000 | Roy et al. ............................ 607/113 |

* cited by examiner

*Primary Examiner*—Carl Layno

(57) ABSTRACT

A hand-held bipolar electrical stimulus probe includes first and second insulated conductors having unequal diameters and a stable side-by-side orientation. The conductors are provided with visually perceptible indicia such as color coding for identification. The conductors are carried within a flexible jacket and the terminal portions thereof are deformable. The conductors are each insulated substantially up to their tips to prevent current shunting. The probe may include a momentary contact switch permitting selective monopolar or bipolar operation.

44 Claims, 3 Drawing Sheets

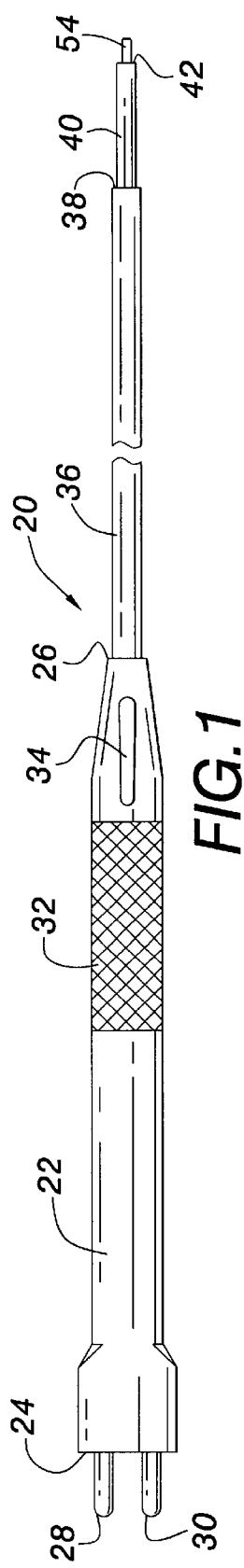
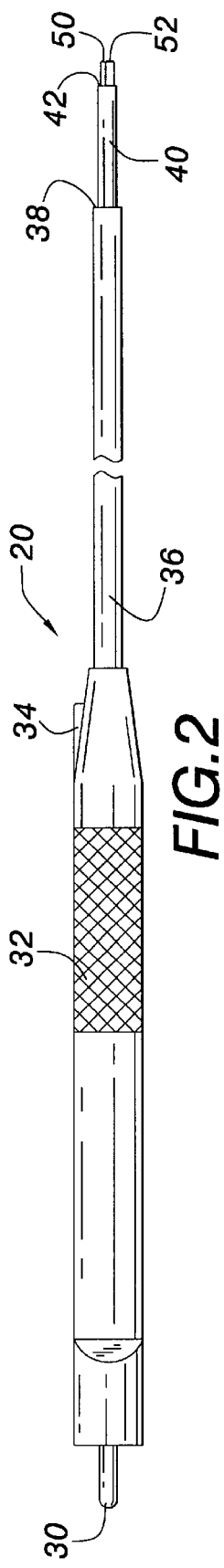
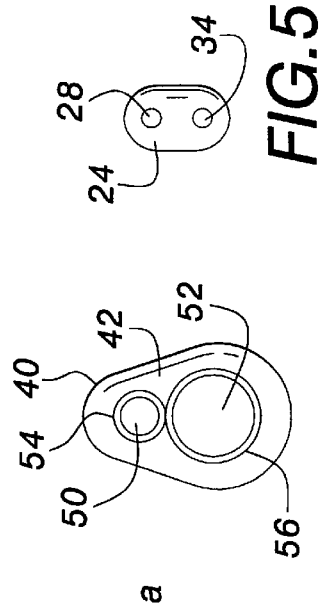
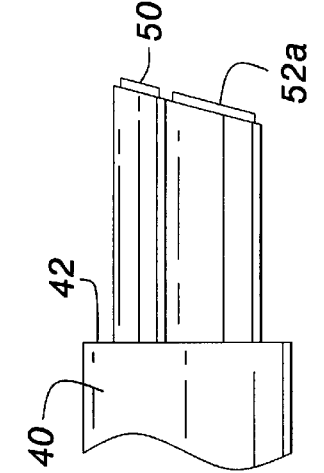
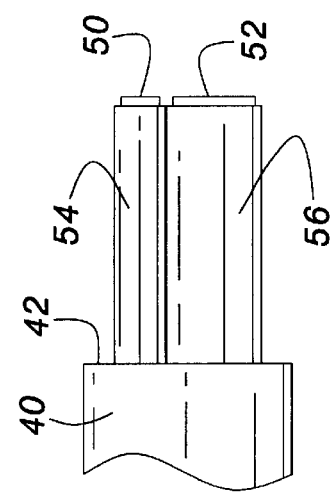

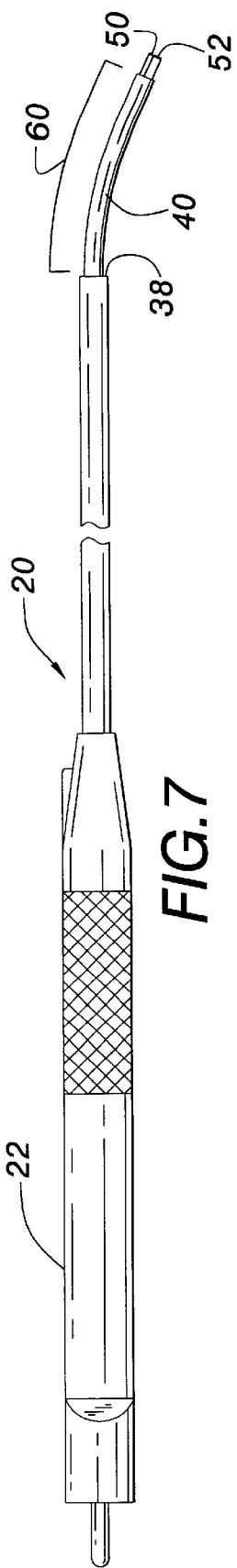
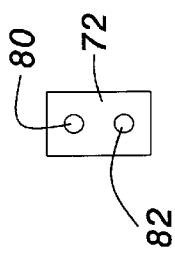
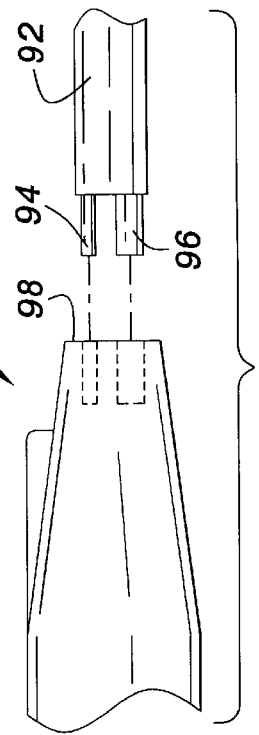
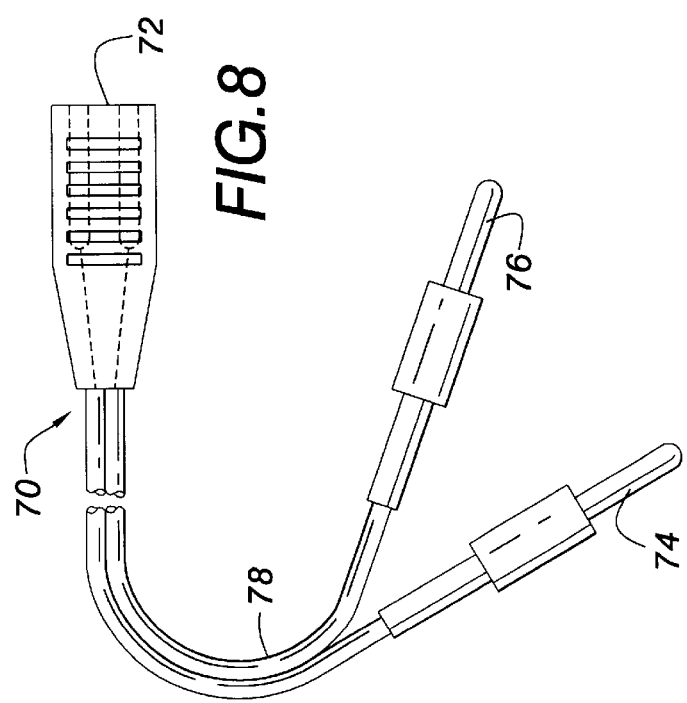
FIG.7
FIG.9
FIG.10
FIG.8

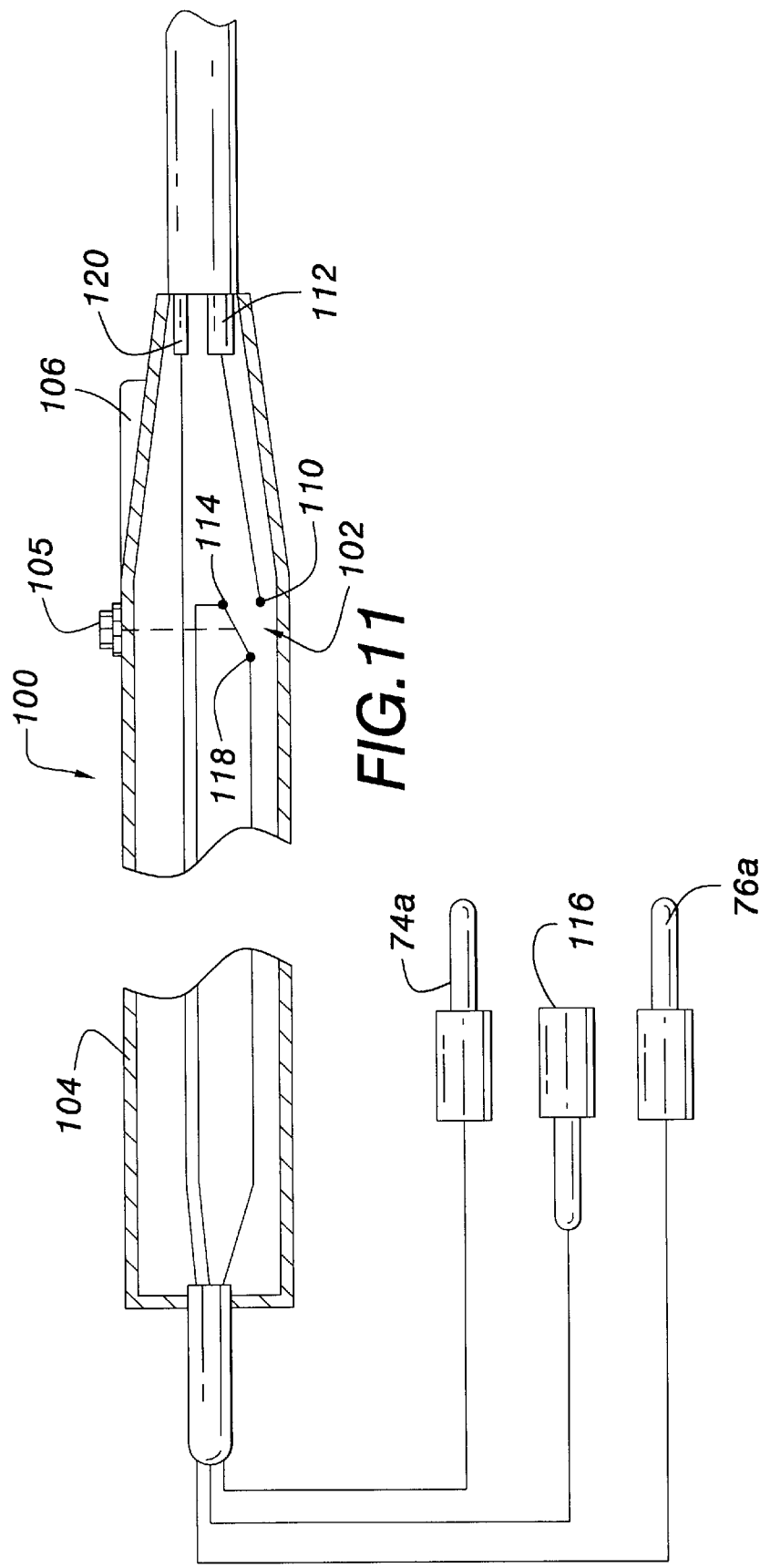

BIPOLAR ELECTRICAL STIMULUS PROBE WITH PLANAR ELECTRODES

CROSS REFERENCE TO RELATED APPLICATION

This application claims benefit from Provisional Application No. 60/096,243, filed Aug. 12, 1998, the entire disclosure of which is incorporated herein by reference.

BACKGROUND OF THE INVENTION

1. Field of the Invention

The present invention relates to surgical apparatus and more particularly to a hand held electrical stimulus probe for use as an intraoperative aid in defining the course of neural structures or in nerve integrity monitoring. The invention is particularly applicable for use in monitoring facial electromyogram (EMG) activity during surgeries in which a facial motor nerve is at risk due to unintentional manipulation and will be described with reference thereto, although it will be appreciated that the invention has broader applications and can be used in other neural monitoring procedures.

2. Discussion of the Prior Art

Despite advancements in diagnosis, microsurgical techniques, and neurotological techniques enabling more positive anatomical identification of facial nerves, loss of facial nerve function following head and neck surgery such as acoustic neuroma resection is a significant risk. Nerves are very delicate and even the best and most experienced surgeons, using the most sophisticated equipment known, encounter a considerable hazard that a nerve will be bruised, stretched or even severed during an operation.

Studies have shown that preservation of the facial nerve during acoustic neuroma resection may be enhanced by the use of intraoperative electrical stimulation to assist in locating nerves. Very broadly stated, the locating procedure, also known as nerve integrity monitoring, involves inserting sensing or recording electrodes directly within cranial muscles controlled by the nerve of interest. An electrical stimulation probe is then applied near the area where the subject nerve is believed to be located. If the stimulation probe contacts or is reasonably near the nerve, the stimulation signal applied to the nerve is transmitted through the nerve to excite the related muscle. Excitement of the muscle causes an electrical impulse to be generated within the muscle; the impulse is transferred to the recording electrodes, thereby providing an indication to the surgeon as to the location of the nerve.

While intraoperative electrical stimulation has been of benefit in localization and preservation of facial nerves during various surgical procedures, the accuracy and reliability of the indication of stimulation depends upon eliminating sources of false indications of stimulation. A major source of false indications of stimulation is the shunting of the electrical stimulus current away from the intended area and through the body fluids. During acoustic neuroma surgery the surgical area is invariably bathed in cerebral spinal fluid (CSF), a clear, colorless body fluid containing electrolytes and capable of conducting electrical current. The earliest stimulus probes were crude segments of uninsulated wire or tapered metal rods touched to the area to be stimulated, often allowing electrical contact with CSF electrolyte fluid, whereupon the electrical stimulus current was allowed to spread along the shunt or parallel paths through the body.

Spreading of the stimulus current reduces the desired electrical current flowing through the nerve tissue intended for stimulation, which may result in false negative indications of stimulation and thus adversely effect the accuracy of the procedure. In the past, others have attempted to compensate for the problem of current stimulus spread by simply increasing the intensity level of the electrical stimulus, whereby the neural response to stimulation occurs despite the current shunted through undesired paths. Increased stimulus current levels increase the possibility of tissue damage, however. In addition, the increased stimulus current may also spread through undesired paths in inactive tissue, reaching the active nerve tissue at a level sufficient to produce a false positive response or indication of stimulation, thus affecting the accuracy of the procedure, as above.

One of the inventors of the present invention addressed current shunting problems in the Electrical Stimulus Probe disclosed in U.S. Pat. No. 4,892,105 (to Richard L. Prass), the entire disclosure of which is incorporated herein by reference. The probe of U.S. Pat. No. 4,892,105 has become known as the Prass Flush-Tip Monopolar Probe and is insulated up to the distal tip to minimize current shunting through undesired paths. The Prass Flush-Tip Monopolar Probe is difficult to use when it is desired to provide a bipolar stimulus, however. Bipolar stimulus is employed whenever it is desired to provide a current path from anode to cathode through desired nerve tissue and at controlled depth into the nerve tissue. In order to provide bipolar stimulus with the Prass Flush-Tip Monopolar Probe, an anode probe and a cathode probe must be placed on or near the nerve and held in place during stimulation; repeatable and consistent placement of the individual monopolar cathode and anode probes must be maintained in order to avoid changes in the detection of the stimulus current, possibly leading to a false response or indication of stimulation, thus affecting the accuracy of the procedure, as above.

Monopolar probes and Bipolar probes (having integral cathode and anode tips) are well suited to specific uses. For most applications of nerve integrity monitoring equipment, the flush tip monopolar probe (having only a cathode) is selected for initial stimulation of motor nerves. In operation, the current spreads out in all directions from the stimulating cathode contact and returns via an anode contact, usually a needle in the patient's shoulder. Current spread increases with increasing current levels and is likely to cause stimulation of any nearby nerve tissue even when the probe cathode contact is not actually touching the nerve or making particular good connection to the nerve. Greater specificity or spatial selectivity can be obtained by operating the probe at reduced levels of stimulus current. At small levels of stimulus current, the nerve is stimulated only when the probe is in direct contact with the neural structure. Accordingly, a balance must be struck since, as stimulation current is decreased, specificity is improved but it is more likely that insufficient current will be provided to stimulate the nerve. At moderate or high levels of monopolar current stimulation, current may be conducted through non-neural tissue at levels adequate to stimulate adjacent neural tissue, causing a false positive response. Moreover, stimulation current may travel through inactive (non-neural) tissue and stimulate motor nerve tissue or adjacent neural structures which may respond simultaneously with the desired neural structure, an undesirable result when seeking to identify a specific motor nerve. Monopolar stimulation at moderate to high current levels is therefore most useful when mapping the course of a selected motor nerve structure but is not well suited when seeking to stimulate a single selected motor nerve in an area of the body having many closely spaced nerve structures, in which case bipolar stimulation is more likely to be effective.

A bipolar stimulating probe offers increased specificity for differentiating adjacent neural structures at moderate to high stimulation current levels. The most important difference between the bipolar stimulation and monopolar stimulation is that current flows directly between cathode and anode tips mounted on the distal end of the bipolar probe instead of going from the monopolar probe cathode to a distant return anode while spreading in all directions from the probe tip. The bipolar probe design permits current flow only from the distal cathode tip to the distal anode tip and therefore primarily stimulates those neural structures between the cathode tip and anode tip. Accordingly, monopolar excitation is preferred when mapping or locating the trajectory of the motor nerves. Once a motor nerve is located, bipolar excitation is preferred for use in differentiating among adjacent nerves.

Others have developed bipolar probes providing an exposed anode conductive tip and an exposed cathode conductive tip, however, the existing bipolar stimulus probes have not proven entirely satisfactory.

Most bipolar probe tips are relatively large to accommodate both a cathode and anode electrode while allowing sufficient inter-electrode distance to ensure adequate penetration of stimulus current into the tissue; there is also a problem of handedness, meaning that a probe may be well suited for use by a left handed or right handed surgeon or for left or right sided surgery, but not both.

Since the insulated probe tips have a specific planar orientation, it may be difficult to accurately place both cathode and anode probe tips flush on the nerve for precisely targeted stimulation. Often, it is desired to malleably flex or plastically deform the probe tips into a more convenient orientation for a given tissue topography, and the bipolar probes of the prior art fail to maintain the preselected anode tip to cathode tip spacing after deformation, thus leading to loss of calibration in the stimulus current, especially in areas within the body having uneven topography.

Additionally, when performing surgery under a microscope it is difficult for the surgeon to determine which tip is the anode and which is the cathode, and so the surgeon may or may not know the direction of current flow during stimulation. The bipolar probes of the prior art also exhibit relatively low efficiency in stimulation of exposed nerve tissue, as compared to monopolar probes.

There is a need, therefore, for an improved method and apparatus for providing bipolar stimulation and/or sensing or recording of electrical activity in the nerve tissue.

OBJECTS AND SUMMARY OF THE INVENTION

Accordingly, it is a primary object of the present invention to overcome the above mentioned difficulties by providing an improved method and apparatus for bipolar stimulation and/or sensing or recording of electrical activity in the nerve tissue.

Another object of the present invention is efficiently delivering bipolar stimulus current to nerve tissue or the like.

Another object of the present invention is providing a hand-held bipolar stimulus probe having cathode and anode conductor tips that are flexible over the terminal or distal portion and stable in side-by-side orientation before and after plastic deformation.

Another object of the present invention is providing a hand-held bipolar stimulus probe having cathode and anode conductor tips with visually perceptible characteristics permitting the surgeon to instantly identify cathode and anode tips.

The aforesaid objects are achieved individually and in combination, and it is not intended that the present invention be construed as requiring two or more of the objects to be combined unless expressly required by the claims attached hereto.

In accordance with the present invention, a hand-held bipolar electrical stimulus probe includes first and second insulated conductors having unequal diameters and a stable side-by-side orientation. It was discovered that by varying the diameter of the cathode and anode conductors, electrical stimulation efficiency was increased. In a first embodiment, the cathode conductor is a relatively small diameter (30 AWG) stainless steel wire and the anode conductor is a larger diameter (24 AWG) stainless steel wire. By providing a smaller cathode wire diameter, current density proximate the cathode (−) conductive surface is increased. The applicants have discovered that the increased cathode (−) current density provides greater current spread and more efficient and effective depolarization and stimulation of the nerve tissue, thereby permitting a repeatable stimulation of the EMG response with greater efficiency and efficacy than was obtainable using the bipolar probes of the prior art. The greater current spread is believed to be attributable to the unequal impedance in the cathode and anode conductors.

The cathode and anode conductors are provided with visually perceptible indicia such as color coding for the cathode insulation, are carried within a flexible jacket and are individually insulated such that the terminal portions (proximate the distal ends) are flexible and malleable or plastically deformable, thereby permitting the surgeon to bend the terminal or distal probe tips into an orientation for more convenient access to neural structures. The flexible jacket maintains the cathode tip to anode tip spacing at a constant or stable distance, both before and after deformation by the surgeon and during use.

The cathode and anode probe conductors each terminate in a substantially planar distal tip surface, also known as a planar conductive surface. The cathode and anode conductors are each insulated substantially up to the tip to prevent current shunting. In the exemplary embodiment illustrated and described in greater detail below, the distance between the cathode and anode planar conductive surfaces is approximately 0.13 mm, for minimal current shunting and greater specificity or directivity in applying the excitation current. This spacing is selected, in part, as a function of insulator thickness. The bipolar probe of the present invention thus permits accurate placement for excitation or monitoring and affords excellent efficiency in electrical stimulation, in a physically compact and visually unobtrusive configuration.

The probe preferably includes a molded plastic handle terminated proximally in first and second electrical connecting pins of differing diameter. The handle carries a distally projecting stainless steel rigid tubular cannula having an axial lumen terminated distally in an open distal end. A flexible plastic molded jacket is carried within the tubular cannula and projects distally from the cannula distal end; the flexible jacket extends distally from the cannula distal end in an unsupported, bendable length of between 0.5 and 1.0 inches, preferably 0.75 inches. Alternatively, the flexible jacket portion extends four fifths of the flexible length that the cathode and anode conductor extend distally beyond the cannula distal end, leaving one fifth of the conductor lengths uncovered by the flexible jacket, whereby the cathode and anode distal tips may be readily viewed.

In the illustrated embodiment, the anode conductor and the cathode conductor project beyond the flexible jacket distal end by a length of approximately 1.8 mm and are terminated in slim, flush cathode and anode tips. By flush is meant that the cathode and anode distal tips are preferably substantially planar conductive surfaces, each insulated substantially up to (or flush with) the terminus.

In the preferred embodiment, the cathode and anode distal ends are disposed in a plane transverse to the probe longitudinal axis. Alternatively, the planar conductive distal ends can be disposed at an acute angle with respect to the longitudinal axis of the probe; in the example disclosed in greater detail below, the cathode planar tip and anode planar tip are disposed in a plane at an angle fifteen degrees from normal with respect to the probe axis.

In another alternative embodiment, the bipolar probe includes a miniature momentary contact single-pole, single-throw switch integrated into the handle. The switch is wired to select either a bipolar anode (on the probe tip) or a remote or distant anode electrode. The probe operates in monopolar mode until the button is pushed in momentary operation whereupon the probe operates in bipolar mode. Selective monopolar or bipolar operation is thereby accomplished using a single stimulus probe. In monopolar mode, only the cathode (i.e. the smaller conductive probe tip) need be in contact with nerve tissue for stimulation. Use of the monopolar mode is desirable when mapping or locating nerve structures or for enhanced penetration of the stimulus current, such as when locating a facial nerve in bone, tumor or in inflammatory tissue, whereas for finer work, such as when discriminating between adjacent nerve structures, bipolar mode is desirable.

The above and still further objects, features and advantages of the present invention will become apparent upon consideration of the following detailed description of a specific embodiment thereof, particularly when taken in conjunction with the accompanying drawings, wherein like reference numerals in the various figures are utilized to designate like components.

BRIEF DESCRIPTION OF THE DRAWINGS

FIG. 1 is a top view of the bipolar electrical stimulus probe of the present invention.

FIG. 2 is a side view of the bipolar electrical stimulus probe of FIG. 1.

FIG. 3 is an enlarged side view of the distal end of the bipolar electrical stimulus probe of FIG. 1.

FIG. 4 is an enlarged end view of the distal end of the bipolar electrical stimulus probe of FIGS. 1, 2 and 3.

FIG. 5 is a proximal end view of the bipolar electrical stimulus probe of FIG. 1.

FIG. 6 is enlarged side view of the distal end of an alternative embodiment of the bipolar electrical stimulus probe of the present invention.

FIG. 7 is a side view of the bipolar electrical stimulus probe of FIG. 1 with a selectively bent terminal portion adjacent the probe distal end.

FIG. 8 is a side view of the bipolar electrical cord for use with the bipolar electrical stimulus probe of the present invention.

FIG. 9 is an end view of the bipolar electrical cord socket connector.

FIG. 10 is an enlarged view of a removable bipolar electrical probe tip.

FIG. 11 is a schematic diagram in partial cross section of an alternative embodiment of the probe of the present invention illustrating the selective operation of the momentary contact switch for use in monopolar/bipolar probe operation.

DESCRIPTION OF THE PREFERRED EMBODIMENT

Referring specifically to FIGS. 1,2, 3, 4 and 5 a bipolar electrical stimulus probe 20 includes an elongate, textured, molded plastic handle 22 having a proximal end 24 opposing a distal end 26. Handle proximal end 24 carries cathode and anode rounded cylindrical electrical connecting pins 28, 30 which project proximally and are spaced apart by a selected spacing. Handle 22 includes a grooved grip area 32 and a transversely projecting salient tactile locator guide 34 aligned along the longitudinal axis of the handle, proximate a tapered distal segment terminating in handle distal end 26 which carries a distally projecting stainless steel rigid hypo tube or cannula 36 having an axial lumen terminated distally in an open distal end 38. Cannula 36 is tapered and preferably has a larger outside diameter proximate the handle distal end 26, tapering to a smaller outside diameter proximate the cannula open distal end 38, with a distally projecting length from handle distal end 26 to cannula distal end 38 encased in clear plastic, thin-wall, shrinkable tubing.

A flexible plastic molded jacket 40 is carried within the tubular cannula 36 and projects distally from the cannula distal end 38. Flexible jacket 40 is preferably made of black ETFE plastic (e.g., such as Dupont TEFZEL 200™ brand ETFE) and extends distally from the cannula distal end 38 in an unsupported, bendable length, terminating in flexible jacket distal end 42. The perimeter of the cross sectional shape of molded jacket 40 includes a first arcuate or semicircular segment having a smaller radius and a second arcuate or semicircular segment having a larger radius, where the first and second arcuate segments are connected by substantially straight tangent lines; the smaller arcuate segment is nearer the smaller cathode tip 50 and the larger arcuate segment is nearer the larger anode tip 52, as best seen in FIG. 4. The molded on jacket 40 thus provides a relatively uniform coating thickness around the cathode and anode conductors.

As best seen in FIGS. 2, 3 and 4, bipolar electrical stimulus probe 20 includes a substantially planar, distally exposed cathode tip 50 and a substantially planar, distally exposed anode tip 52 in a coplanar configuration with cathode tip 50. Cathode tip 50 is the distal end of an elongate cathode conductor having electrical continuity with handle cathode pin 28 and anode tip 52 is the distal end of an elongate anode conductor having electrical continuity with handle anode pin 30. The cathode conductor is insulated in enveloping black plastic (e.g., PFA) wire insulation 54 extending substantially up to the distal end of cathode tip 50 and the anode conductor is insulated in enveloping clear plastic (e.g., PFA) wire insulation 56 extending substantially up to the distal end of anode tip 52 (as best seen in FIG. 3), thus, the conductors are provided with visually perceptible indicia (e.g., color coding) for cathode and anode identification. When viewed under a microscope, the surgeon can readily distinguish the black insulation 54 as identifying the cathode conductor; the applicant has discovered that black PVA insulation is particularly well suited to providing a high contrast visual identifying indicia for cathode (or anode) electrodes used in surgical procedures viewed under a microscope.

The cathode conductor and the anode conductor project beyond the flexible jacket distal end 42 by a length of approximately 1.8 mm and are terminated in slim, flush cathode and anode tips 50, 52. By flush is meant that the cathode and anode distal tips 50, 52 are preferably substantially coplanar conductive surfaces, each insulated substantially up to (or flush with) the tips to prevent current shunting. Cathode tip 50 and anode tip 52 have different or unequal diameters and are fixed in a stable side-by-side (or top and bottom) orientation with spacing therebetween being controlled by jacket 40. It was discovered that by varying the diameter of the cathode and anode conductors, or at least the tip diameters, electrical stimulation efficiency was increased. In the embodiment of FIGS. 1, 2, 3 and 4, the cathode conductor is a 30 AWG stainless steel wire with an outside diameter of approximately 0.230 mm and the anode conductor is a 24 AWG stainless steel wire with an outside diameter of approximately 0.460 mm. By providing a smaller cathode wire diameter, current density proximate the cathode (−) conductive tip surface is increased. The applicants have discovered that the increased cathode (−) current density provides more efficient and effective depolarization and stimulation of the nerve tissue, thereby permitting a repeatable stimulation of the EMG response with greater efficacy than was obtainable using the bipolar probes of the prior art. Conversely, applicants observed that when the cathode and anode leads were switched, thereby making the anode tip smaller than the cathode tip, less efficient stimulation was observed at identical stimulus current intensity settings.

Transversely projecting locator guide 34 serves as a tactile salient feature aligned with the cathode conductor, thus allowing the surgeon to use a finger to orient the probe with the cathode conductor tip 50 in a desired angular direction.

As best seen in FIGS. 3 and 4, the spacing or distance between the cathode and anode planar conductive surfaces is approximately 0.13 mm; narrow spacing tends to minimize current shunting and provide greater specificity or directivity in applying the excitation current. The bipolar probe of the present invention thus permits accurate placement for excitation or monitoring and affords excellent efficiency in electrical stimulation, in a physically compact configuration.

In the preferred embodiment as shown in FIG. 3, the substantially planar cathode and anode distal tips 50, 52 are disposed in a plane transverse to the probe longitudinal axis.

In an alternative embodiment illustrated in FIG. 6, a planar conductive distal cathode tip 50*a* and planar conductive anode tip 52*a* are disposed at an acute angle with respect to the longitudinal axis of the probe. Cathode planar tip 52*a* and anode planar tip 54*a* are disposed in a plane at an angle of approximately fifteen degrees from normal with respect to the probe axis.

FIG. 7 is a side view of the bipolar electrical stimulus probe of FIG. 1 with a selectively bent terminal portion proximate the distal end. The unsupported bendable terminal portion 60 of the probe 20 comprises the length of flexible jacket (and cathode and anode conductors) extending distally beyond the rigid cannula tube distal end 38. The choice of materials determines the ideal unsupported length for the terminal portion which, in accordance with the present invention, is malleable or plastically deformable to retain the shape imparted by the surgeon in bending and adapting the probe for use in a particular surgery, as best seen in FIG. 7. During a surgical procedure, the surgeon places the probe distal cathode tip 50 and anode tip 52 against subcutaneous tissue such as nerve tissue and applies axial compressive force to maintain electrical contact between the tissue and the tips 50, 52. The length, stiffness, resiliency and memory characteristics of the materials selected for use in probe terminal portion 60 (including the cathode wire and anode wire) allow the terminal portion to resiliently retain the selected bent shape and have sufficient rigidity to provide resilient resistance to bending or buckling when in operable contact with subcutaneous tissue such as nerve tissue. The applicants determined experimentally that it was especially difficult to keep the spacing of differently sized cathode and anode conductors constant or stable during and after deformation by the surgeon and during use. The applicant's solution to the problem of stability is providing the thin, flexible jacket or insulator sleeve 40 extending distally from the inflexible cannula distal end 38 for a length of at least four fifths of the length of the terminal portion 60; thereby leaving adequate flexibility and visibility of the tissue contacting distal tips 50, 52.

FIG. 8 is a side view of the bipolar electrical cord 70 for use with the bipolar electrical stimulus probe 22; electrical cord 70 has a distal dual socket connector 72 providing continuity to first and second proximal two mm diameter connector pins 74, 76, via a selected length (e.g., approximately two meters) of flexible, 24 AWG, two-conductor, unshielded duplex wire 78. When in use, connectors 74 and 76 are plugged into corresponding sockets in a patient interface module of a nerve integrity monitoring instrument (such as the Xomed® NIM-2® XL Nerve Integrity Monitor). FIG. 9 is an end view of the bipolar electrical cord socket connector 72 and shows the cathode socket 80 having a diameter of 0.062 inches and the anode socket 82 having a diameter of 0.072 inches; the cathode and anode sockets 80, 82 are sized to receive and provide an electrical connection with the probe connector pins 28, 30.

FIG. 10 is an enlarged view of an embodiment of the bipolar probe including a removable bipolar electrical probe portion 92 including a cathode pin connection 94 and an anode pin connection 96 shown withdrawn from corresponding cathode and anode socket connections in the distal end 98 of the handle.

In the preferred embodiment of the probe of the present invention, cathode and anode rounded cylindrical electrical connecting pins 28, 30 are spaced approximately 0.220 inches apart. Cathode pin 28 has a diameter of 0.062 inches and a length of 0.30 inches, anode pin 30 has a diameter of 0.072 inches and a length of 0.30 inches. Handle 22 has an axial length of 3.88 inches and transversely projecting salient tactile locator guide 34 is aligned along the longitudinal axis of the handle, proximate the tapered distal segment terminating in handle distal end 26 which carries a distally projecting stainless steel rigid hypo tube or cannula 36 having an axial lumen terminated distally in an open distal end 38. Cannula 36 tapers with an outside diameter of 0.13 inches proximate the handle distal end 26, has an outside diameter of 0.080 inches proximate the cannula open distal end 38 and has a distally projecting length from handle distal end 26 to cannula distal end 38 of approximately 2.3 inches.

Flexible jacket 40 is preferably made of black ETFE plastic (e.g., such as Dupont TEFZEL 200™ brand ETFE) and extends distally from the cannula distal end 38 in an unsupported, bendable length of between 0.5 and 1.0 inches, preferably 0.75 inches.

FIG. 11 is a schematic diagram in partial cross section of an alternative embodiment of the probe of the present invention including an anode selective bipolar probe 100 incorporating a miniature momentary contact single throw, single pole, three terminal switch 102 for selective use enabling both monopolar and bipolar modes of probe operation. The anode selective bipolar probe 100 preferably includes a malleable terminal portion having a cathode tip and anode tip with the same geometry and dimensions as specified for the bipolar probe of FIGS. 1–4.

The momentary contact switch 102 is integrated into the probe handle 104 and is actuated by a button 105 preferably located adjacent the handle locator guide 106. The three terminals of switch 102 are wired with a first terminal 110 connected to the probe anode conductor 112. The second switch terminal 114 is connected to a remote anode 116 which is positioned against the patient's body, as is customarily done in monopolar excitation. The third switch terminal 118 is connected to anode connector pin 74*a*. Cathode connector pin 76*a* is hard wired to the cathode conductor 120 and is not affected by operation of switch 102. Connector pins 74*a* and 76*a* are adapted for connection to corresponding sockets in the patient interface module of a nerve integrity monitoring instrument, as above.

Momentary contact switch 102 is wired to select either the probe tip anode, for bipolar probe operation, or remote anode electrode 116, for monopolar probe operation. Anode selective bipolar probe 100 operates in monopolar mode until button 105 is pushed in momentary operation. Selective monopolar or bipolar operation is thereby accomplished using a single anode selective bipolar probe 100. In monopolar mode, only the cathode (i.e. the smaller conductive probe tip) need be in contact with nerve tissue for stimulation.

When used for head and neck monitoring with nerve integrity monitoring equipment, the monopolar mode is selected (by not depressing button 105) and the stimulus current spreads out in all directions from the stimulating cathode contact and returns via the anode contact 116 (e.g., a needle electrode in the patient's shoulder such as is disclosed in U.S. Pat. No. 5,161,533, to Prass, et al, the entire disclosure of which is incorporated herein by reference). Current spread increases with increasing current levels and will likely cause stimulation of nerve tissue even when the probe cathode tip is not actually touching the nerve or making particular good connection to the nerve. At moderate or high levels of monopolar current stimulation, adjacent neural structures may respond simultaneously with the desired neural structure. Use of the monopolar mode of stimulation at moderate to high current levels is therefore most useful when mapping the course of a selected motor nerve structure but is not well suited when seeking to stimulate a single selected motor nerve in an area of the body having many closely spaced motor nerve structures, in which case use of the bipolar stimulation mode is more likely to be effective.

The bipolar mode of operation offers increased specificity for differentiating adjacent neural structures at moderate to high stimulation current levels, and is accomplished by depressing button 105 on the handle of anode selective bipolar probe 100. The most important difference between the bipolar mode of stimulation and the monopolar mode of stimulation is that current flows directly between the two tips of probe 100 instead of going from the probe cathode to the remote return anode 116 and spreading at all directions. The bipolar mode of excitation permits current flow only from the probe distal cathode tip to the probe distal anode tip and therefore stimulates only those neural structures between the cathode tip and anode tip. Accordingly, monopolar excitation is preferred when mapping of locating the trajectory of the motor nerves, and once a motor nerve is located, bipolar excitation is preferred for use in differentiating among adjacent nerves.

In an alternative embodiment adapted for direct recording of compound nerve action potentials from sensory nerves, motor nerves or brain tissue; greatest spacial selectivity may be obtained with a bipolar probe structure having anode and cathode electrodes of equal diameter.

Having described preferred embodiments of a new and improved method, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A hand-held instrument for monitoring or electrically stimulating exposed, subcutaneous tissue of a living body, comprising:

an elongate cannula having an open proximal end, an open distal end and a lumen there between;

a handle carried on said cannula proximal end;

an elongate cathode conductor including a proximal end and a distal end having a distal end surface having a first diameter, said cathode conductor having sufficient rigidity to provide resistance to bending when in operable contact with subcutaneous tissue;

said cathode conductor being disposed within a first flexible insulating sheath;

an elongate anode conductor including a proximal end and a distal end having a planar distal end surface having a second diameter larger than said cathode conductor distal end first diameter, said anode conductor having sufficient rigidity to provide resilient resistance to bending when in operable contact with subcutaneous tissue;

said anode conductor being disposed within a second flexible insulating sheath;

said cathode conductor and said anode conductor being carried within said cannula lumen, wherein said cathode conductor distal end and said anode conductor distal end project distally beyond said cannula open distal end.

2. The hand-held instrument of claim 1, said first flexible insulating sheath including a colored surface.

3. The hand-held instrument of claim 2, said first flexible insulating sheath including a black surface.

4. The hand-held instrument of claim 1, said cathode conductor and said anode conductor being carried within an elongate non-conductive, flexible jacket having a distal end, wherein said cathode conductor distal end and said anode conductor distal end project distally beyond said jacket distal end; and said flexible jacket, cathode conductor and said anode conductor being carried within said cannula lumen, wherein said flexible jacket distal end, said cathode conductor distal end and said anode conductor distal end project distally beyond said cannula open distal end.

5. The hand-held instrument of claim 4, said flexible segment extending beyond said cannula distal end in an unsupported malleable length; said jacket unsupported malleable length being in the range of one half inch to one inch.

6. The hand-held instrument of claim 1, wherein said cathode and anode distal end surfaces lie in a plane disposed at an angle to the elongate cathode conductor axis.

7. The hand-held instrument of claim 6, wherein said plane is disposed at an angle fifteen degrees from normal to the elongate cathode conductor axis.

8. A hand-held instrument for monitoring or electrically stimulating exposed, subcutaneous tissue of a living body, comprising:
   an elongate cannula having an open proximal end, an open distal end and a lumen there between;
   a handle carried on said cannula proximal end;
   an elongate, flexible, cathode conductor including a proximal end and a distal end having a substantially planar distal end surface, said cathode conductor being malleably deformable and having sufficient resilience to resist bending when in operable contact with subcutaneous tissue;
   said cathode conductor being disposed within a first flexible insulating sheath extending distally to and substantially flush with the distal end of said cathode conductor, said sheath leaving said cathode conductor planar distal end surface exposed;
   an elongate, flexible anode conductor including a proximal end and a distal end having a planar distal end surface, said anode conductor being malleably deformable and having sufficient resilience to resist bending when in operable contact with subcutaneous tissue;
   said anode conductor being disposed within a second flexible insulating sheath extending distally to and substantially flush with the distal end of said anode conductor, said sheath leaving said anode conductor planar distal end surface exposed;
   wherein at least one of said cathode conductor and said anode conductor include visible identifying indicia; and
   said cathode conductor and said anode conductor being carried within said cannula lumen, wherein said cathode conductor distal end and said anode conductor distal end project distally beyond said cannula open distal end.

9. The hand-held instrument of claim 8, said visible identifying indicia comprising a color coded flexible insulating sheath.

10. The hand-held instrument of claim 9, said color coded flexible insulating sheath comprising a black plastic insulating sheath disposed on said cathode conductor.

11. The hand-held instrument of claim 10, said handle further including a tactile salient feature aligned with said cathode conductor.

12. A hand-held instrument for monitoring or electrically stimulating exposed, subcutaneous tissue of a living body, comprising:
   a handle having a proximal end and a distal end;
   an elongate, flexible, cathode conductor including a proximal end and a distal end having a distal end surface, said cathode conductor having sufficient resilience to resist bending when in operable contact with subcutaneous tissue;
   said cathode conductor being disposed within an insulating sheath, said sheath leaving said cathode conductor distal end surface exposed;
   an elongate, flexible anode conductor including a proximal end and a distal end having a distal end surface, said anode conductor having sufficient resilience to resist bending when in operable contact with subcutaneous tissue;
   said anode conductor being disposed within an insulating sheath, said sheath leaving said anode conductor distal end surface exposed;
   said handle further including a switch having first and second terminals; said first switch terminal being connected to one of said cathode conductor and said anode conductor; and
   said cathode conductor and said anode conductor being carried by said handle, wherein said cathode conductor distal end and said anode conductor distal end project distally beyond said handle distal end.

13. The hand-held instrument of claim 12, said first switch terminal being connected to said anode conductor.

14. The hand-held instrument of claim 13, further including a remote anode electrode;
   said second switch terminal being connected to said remote anode electrode.

15. The hand-held instrument of claim 14, said switch being actuable by a pushbutton carried externally on said handle.

16. The hand-held instrument of claim 12, said switch being a momentary contact, single-pole single-throw switch.

17. The hand-held instrument of claim 10, wherein said instrument operates in a bipolar mode when said switch is actuated.

18. An instrument for monitoring or electrically stimulating exposed, subcutaneous tissue of a living body, comprising:
   an elongate cathode conductor including a proximal end and a distal end having a distal end surface, said cathode conductor having sufficient resilience to resist bending when in operable contact with subcutaneous tissue, said cathode conductor having a diameter;
   said cathode conductor being disposed within a first insulating sheath, said first sheath extending substantially to the cathode conductor distal end and leaving said cathode conductor distal end surface exposed;
   said cathode conductor distal end surface defining a substantially planar distally exposed cathode tip;
   an elongate anode conductor including a proximal end and a distal end having a distal end surface, said anode conductor having sufficient resilience to resist bending when in operable contact with subcutaneous tissue, said anode conductor having a diameter different from said diameter of said cathode conductor;
   said anode conductor being disposed within a second insulating sheath, said second sheath extending substantially to the anode conductor distal end and leaving said anode conductor distal end surface exposed; and
   said anode conductor distal end surface defining a substantially planar distally exposed anode tip, wherein said substantially planar distally exposed anode tip and said substantially planar distally exposed cathode tip are in a substantially coplanar flush distal tip configuration.

19. The instrument of claim 18, said cathode conductor including a selectively bendable malleable terminal portion proximate said distal end, said malleable portion adapted to resiliently retain a selected bent shape;
   said anode conductor including a selectively bendable malleable terminal portion proximate said distal end, said malleable portion adapted to resiliently retain a selected bent shape; and
   said cathode and anode conductors being disposed in a flexible jacket, said jacket extending over a selected fraction of the length of the cathode and anode malleable terminal portion and maintaining a selected spacing between said flush distal tips of said anode and cathode conductors.

20. The instrument of claim 18, said cathode conductor having a first diameter and said anode conductor having a second diameter larger than said first diameter.

21. An instrument for monitoring or electrically stimulating exposed, subcutaneous tissue of a living body, comprising:
   an elongate cathode conductor including a wire having a proximal end and a distal end having a distal end surface, said wire of said cathode conductor having sufficient resilience to resist bending when in operable contact with subcutaneous tissue;
   said wire of said cathode conductor being malleable along a selectively bendable malleable terminal portion proximate said distal end, said malleable terminal portion being adapted to resiliently retain a selected bent shape;
   an elongate anode conductor including a wire having a proximal end and a distal end having a distal end surface, said wire of said anode conductor having sufficient resilience to resist bending when in operable contact with subcutaneous tissue;
   said wire of said anode conductor being malleable along a selectively bendable malleable terminal portion proximate said distal end of said wire of said anode conductor, said malleable terminal portion of said anode conductor being adapted to resiliently retain a selected bent shape; and
   said wires being sheathed in a flexible jacket, said jacket extending over a selected fraction of the length of said malleable terminal portions and maintaining a selected side by side spacing between said distal end surfaces of said wires.

22. The instrument of claim 21, said flexible jacket extending over four-fifths of said malleable terminal portions.

23. The instrument of claim 21, said wire of said cathode conductor having a first diameter and said wire of said anode conductor having a second diameter larger than said first diameter.

24. The instrument of claim 21, said wire of said cathode conductor carrying an insulating sheath having a first color and said wire of said anode conductor carrying an insulating sheath having a second color visually distinguishable from said first color.

25. The instrument of claim 21, said cathode conductor distal end surface defining a substantially planar exposed cathode tip and said anode conductor distal end surface defining a substantially planar exposed anode tip in a substantially coplanar, flush distal tip configuration with said cathode tip.

26. An instrument for monitoring or electrically stimulating exposed, subcutaneous tissue of a living body, comprising:
   an elongate cathode conductor including a proximal end and a distal end having a distal end surface, said cathode conductor having sufficient resilience to resist bending when in operable contact with subcutaneous tissue;
   an elongate anode conductor including a proximal end and a distal end having a distal end surface, said anode conductor having sufficient resilience to resist bending when in operable contact with subcutaneous tissue;
   said cathode conductor having a first diameter and said anode conductor having a second diameter different than said cathode first diameter.

27. The instrument of claim 26, said anode conductor second diameter being larger than said cathode first diameter.

28. The instrument of claim 27, said anode conductor second diameter being approximately twice said cathode conductor first diameter.

29. The instrument of claim 27, said anode conductor second diameter being 24 AWG and said cathode conductor first diameter being 30 AWG.

30. The instrument of claim 26, said cathode conductor carrying an insulating sheath having a first color and said anode conductor carrying an insulating sheath having a second color visually distinguishable from said cathode insulating sheath first color.

31. The instrument of claim 26, said cathode conductor distal end surface defining a substantially planar exposed cathode tip and said anode conductor distal end surface defining a substantially planar exposed anode tip in a substantially coplanar, flush distal tip configuration with said cathode tip.

32. The instrument of claim 26, further including a bipolar electrical cord having first and second flexible conductors, said first flexible conductor having a first diameter and said second flexible conductor having a second diameter different than said first flexible conductor first diameter.

33. A hand-held instrument for monitoring or electrically stimulating exposed, subcutaneous tissue of a living body, comprising:
   an elongate cannula having an open proximal end, an open distal end and a lumen there between;
   a handle carried on said proximal end;
   a flexible, non-conductive, elongate jacket projecting distally from said cannula distal end to terminate at a jacket distal end;
   an elongate, flexible cathode conductor disposed within said jacket and extending distally from said cannula distal end to terminate at a cathode conductor distal end disposed distally of said jacket distal end, said cathode conductor distal end having a planar distal end surface, said cathode conductor being malleably deformable and having sufficient resilience to resist bending when in operable contact with subcutaneous tissue;
   said cathode conductor being disposed within a first flexible insulating sheath extending distally from said jacket distal end to terminate substantially flush with said distal end of said cathode conductor, said first sheath leaving said cathode conductor planar distal end surface exposed;
   an elongate, flexible anode conductor disposed within said jacket and extending distally from said cannula distal end to terminate at an anode conductor distal end disposed distally of said jacket distal end, said anode conductor distal end having a planar distal end surface, said anode conductor being malleably deformable and having sufficient resilience to resist bending when in operable contact with subcutaneous tissue; and
   said anode conductor being disposed within a second flexible insulating sheath extending distally from said jacket distal end to terminate substantially flush with said distal end of said anode conductor, said second sheath leaving said anode conductor planar distal end surface exposed.

34. The hand-held instrument of claim 33, said anode conductor and said cathode conductor in said flexible jacket defining a malleable distal probe segment; said malleable distal probe segment being plastically deformable to a selected angular position, wherein said malleable distal probe segment will, after deformation, resiliently maintain said selected angular position.

35. The hand-held instrument of claim 34, wherein said distal probe segment has a length in the range of one half inch to one inch.

36. The hand-held instrument of claim 35, wherein said length is three quarters of an inch.

37. The hand-held instrument of claim 33, said elongate cathode conductor having a first diameter.

38. The hand-held instrument of claim 37, said elongate anode conductor having a second diameter larger than said first diameter.

39. The hand-held instrument of claim 37, wherein said cathode and anode planar distal end surfaces lie in a plane disposed at an angle to the elongate cathode conductor axis.

40. The hand-held instrument of claim 39, wherein said plane is disposed at an angle fifteen degrees from normal to the elongate cathode conductor axis.

41. A hand-held instrument for monitoring or electrically stimulating exposed, subcutaneous tissue of a living body, comprising:

an elongate cannula having an open proximal end, an open distal end and a lumen there between;

a handle carried on said cannula proximal end;

an elongate, flexible, cathode conductor including a proximal end and a distal end having a substantially planar distal end surface, said cathode conductor being malleably deformable and having sufficient resilience to resist bending when in operable contact with subcutaneous tissue, said elongate cathode conductor having a first diameter;

said cathode conductor being disposed within a first flexible insulating sheath extending distally to and substantially flush with said distal end of said cathode conductor, said first sheath leaving said cathode conductor planar distal end surface exposed, said first sheath including a colored surface;

an elongate, flexible anode conductor including a proximal end and a distal end having a planar distal end surface, said anode conductor being malleably deformable and having sufficient resilience to resist bending when in operable contact with subcutaneous tissue;

said anode conductor being disposed within a second flexible insulating sheath extending distally to and substantially flush with said distal end of said anode conductor, said second sheath leaving said anode conductor planar distal end surface exposed;

said cathode conductor and said anode conductor being carried within an elongate non-conductive, flexible jacket having a distal end, wherein said cathode conductor distal end and said anode conductor distal end project distally beyond said jacket distal end; and said flexible jacket, said cathode conductor and said anode conductor being carried within said cannula lumen, wherein said flexible jacket distal end, said cathode conductor distal end and said anode conductor distal end project distally beyond said cannula open distal end.

42. The hand-held instrument of claim 41, said first flexible insulating sheath including a black surface.

43. An instrument for monitory or electrically stimulating exposed, subcutaneous tissue of a living body, comprising:

an elongate cathode conductor including a proximal end and a distal end having a distal end surface, said cathode conductor having sufficient resilience to resist bending when in operable contact with subcutaneous tissue;

said cathode conductor being disposed within a first insulating sheath, said first sheath extending substantially to the cathode conductor distal end and leaving said cathode conductor distal end surface exposed, said first sheath having a first color;

said cathode conductor distal end surface defining a substantially planar distally exposed cathode tip;

an elongate anode conductor including a proximal end and a distal end having a distal end surface, said anode conductor having sufficient resilience to resist bending when in operable contact with subcutaneous tissue;

said anode conductor being disposed within a second insulating sheath, said second sheath extending substantially to the anode conductor distal end and leaving said anode conductor distal end surface exposed, said second sheath having a second color visually distinguishable from said first color; and said anode conductor distal end surface defining a substantially planar distally exposed anode tip, wherein said substantially planar distally exposed anode tip and said substantially planar distally exposed cathode tip are in a substantially coplanar flush distal tip configuration.

44. A method for depolarization and stimulation of nerve tissue, providing repeatable stimulation with greater efficacy, comprising a) providing an anode having a first selected wire diameter and a cathode with a second wire diameter smaller than said anode wire diameter, wherein the current density proximate the cathode conductive tip surface is greater than the current density proximate the anode tip; and b) stimulating the nerve tissue with said cathode and said anode.

* * * * *